United States Patent [19]

Dölling et al.

[11] Patent Number: 5,196,417
[45] Date of Patent: Mar. 23, 1993

[54] PIROXICAM-CONTAINING PHARMACEUTICAL COMPOSITION FOR TOPICAL USE

[75] Inventors: Reinhold Dölling, Feldkirchen-Westerham; Uwe N. Johann, München, both of Fed. Rep. of Germany

[73] Assignee: Sagitta Arzneimittel GmbH, Feldkirchen-Westerham, Fed. Rep. of Germany

[21] Appl. No.: 604,677

[22] Filed: Oct. 26, 1990

[30] Foreign Application Priority Data

Apr. 4, 1990 [EP] European Pat. Off. ........ 90107992.1

[51] Int. Cl.$^5$ .............................................. A61K 31/54
[52] U.S. Cl. .................................. 514/226.5; 514/937
[58] Field of Search ...................................... 514/226.5

[56] References Cited

U.S. PATENT DOCUMENTS

| | | | |
|---|---|---|---|
| 4,623,346 | 11/1986 | von Bitters et al. | 604/897 |
| 4,627,852 | 12/1986 | von Bitters et al. | 604/897 |
| 4,661,104 | 4/1987 | von Bitters et al. | 604/896 |
| 4,678,666 | 7/1987 | Nowaza et al. | 424/81 |
| 4,824,841 | 4/1985 | Chiesi et al. | 514/226.5 |

FOREIGN PATENT DOCUMENTS

| | | |
|---|---|---|
| 0101178 | 7/1983 | European Pat. Off. . |
| 0331382 | 2/1989 | European Pat. Off. . |

OTHER PUBLICATIONS

Chemical Abstracts 103: 11362r (1985).

*Primary Examiner*—Leonard Schenkman
*Attorney, Agent, or Firm*—Pravel, Gambrell, Hewitt, Kimball & Krieger

[57] ABSTRACT

A pharmaceutical composition for topical application is described on the basis of a W/O emulsion, which contains piroxicam in the oil phase as an active ingredient. On account of its good compatibility to the skin and stability characteristics, the composition is very suitable for use as an antirheumatic, antiphlogistic and/or anti-inflammatory pharmaceutical.

30 Claims, No Drawings

PIROXICAM-CONTAINING PHARMACEUTICAL COMPOSITION FOR TOPICAL USE

CROSS REFERENCE TO RELATED APPLICATIONS

This is a U.S. Application based on European Patent Application No. 90 107 992.1, filed Apr. 4, 1990, which is hereby incorporated by reference for all purposes.

FIELD OF THE INVENTION

The invention relates to a piroxicam-containing pharmaceutical composition for topical use in the case of diseases and injuries of the locomotive system (sport injuries, rheumatic morphic cycle).

BACKGROUND OF THE INVENTION

Piroxicam (4-hydroxy-2-methyl-N-2-pyridyl-2H-1,2-benzothiazine-3-carboxamide-1, 1-dioxide), a substance belonging to the group of oxicams (dihydrothiazine derivatives) has been known for many years as a non-steroidal antirheumatic agent/antiphlogistic agent (NSAR) and analgesic, e.g. for injuries and tooth extractions (see DE-PS 1943265). In spite of its high efficacy and long-duration effect, its oral application is however accompanied by the side-effects of NSAR, such as gastrointestinal haemorrhage, damage to the heart and kidney function (see e.g. "Pharmazie in unserer Zeit 13 (1984) 177, 185).

In order to avoid or reduce side effects, it is therefore desirable to supplement the oral application by a topical application, especially in the case of localized injuries or diseases of the locomotive system.

For a topical application, i.e. administration on and through the skin over a longer period of time, medicinal plasters were proposed which contain an antiphlogistic agent as an effective substance (see DE-A-3344691, 3347277, 3347278).

EP-A-0331382 describes compositions for transdermal application having an increased transdermal flow, which contain besides the effective substance, e.g. piroxicam, and an aqueous solvent system, a penetration-enhancing agent from the group of the 1-alkyl azacycloheptane-2-ones.

From the Japanese published patent application JP 5913714 (8413714), piroxicam-containing anti-inflammatory and analgesic compositions are known, e.g. in the form of an ointment with an oil in water (O/W) ointment base, which contains carboxyvinyl polymer, ethanol, propylene-glycol, diethanolamine, 2-hydroxyethyl cellulose ether, polyvinyl pyrrolidone and water.

EP-B-0101178 describes a topical, antiphlogistic drug in the form of a gel-ointment in an aqueous system, which contains an effective, antiphlogistic amount of piroxicam, 10 to 50% by wt. of a lower alkanol, a gel-forming amount of carboxyvinyl polymer, 5 to 40% by weight of a multivalent alcohol and an amount rendering piroxicam soluble of at least one alkanol amine in water.

Such formulations of non-steroidal antirheumatic agents, such as e.g. piroxicam, for the topical application in hydrophilic bases, such as e.g. the above-named oil-in-water gel- ointment form, or gels which contain the piroxicam in propylene glycol, ethyl- and isopropyl alcohol, have the advantage that as systems dilutable with water they can be easily washed off; moreover they have no smell and are non-greasy.

Piroxicam forms a monohydrate with lemon-yellow color. This hydrate is less soluble than piroxicam, so that aqueous solutions of piroxicam in the pH-range of about 2-8 are to be regarded as metastable in the respect that yellow piroxicam monohydrate can crystallize out of them. The known formulations containing piroxicam in hydrophilic bases, such as e.g. O/W creams suitable for topical application, therefore have the disadvantage that upon a longer storage time, on account of the property of piroxicam to convert into the yellow monohydrate, they turn yellow. On account of this instability, and also on account of the unattractive optical appearance caused by the discoloring, these formulations are frequently rejected by the consumer.

EP- A- 0179430 describes a piroxicam-containing preparation, in which the yellow piroxicam monohydrate is incorporated in an O/W cream.

Formulations in hydrophilic bases generally have the characteristic that the effective substance is administered well to the skin.

The formulations on the basis of hydrophilic bases for topical use, such as gels or O/W creams, have the disadvantage, however, that they lead to a desiccation of the skin.

SUMMARY OF THE INVENTION

It is the object of the present invention to provide a piroxicam-containing pharmaceutical composition for topical use which no longer has the above-indicated disadvantages (discoloring on account of instability, desiccation of the skin), which has a good stability over a longer period of time, and is suitable in an easy and reproducible manner for external application on the skin.

It has now been found that this object can be solved by a composition which contains the effective substance in a lipophilic water-in-oil (W/O) system.

The subject matter of the invention is therefore a pharmaceutical composition according to claim 1 for topical application on the basis of a water-in-oil (W/O) emulsion, which is characterized in that it contains piroxicam as an effective substance in the oil phase, and optionally means for the stabilization, conservation and/or usual pharmaceutical non-active ingredients and/or carriers.

DESCRIPTION OF THE INVENTION

The composition according to the invention on the basis of a water-in-oil emulsion contains the piroxicam in the fatty phase; by direct incorporation in the fatty phase, it is possible in this manner to separate the piroxicam rapidly from water, resulting in a preparation possessing excellent long-time stability. In comparison to until now customary piroxicam-containing preparations for topical application, the preparations according to the invention have at least an equally good antirheumatic/antiinflammatory efficacy; by the incorporation of penetration- enhancing agents, the skin resorption can be optimized. The pharmaceutical preparations according to the invention, e.g. in the form of a cream, do not reveal any optical change, e.g. yellowing, due to their excellent long-time stability. They do not tend to cause scale formation or an allergic appearance even after prolonged application. The skin-care characteristics are as a rule superior to those of an O/W-system.

The composition according to the invention on the basis of a water-in-oil emulsion can take the form of an ointment, cream, paste or emulsion, the transition between these forms being fluent; according to the customary definitions, the composition according to the invention contains, when it takes the form of a paste, e.g. also powdery components, e.g. suitable pharmaceutical auxiliary ingredients and/or additives (for the definition and for differentiation of the above-named terms, see Rommp's "Chemie Lexikon", 8th revised edition, page 3661).

As components building up the fatty phase, the fatty phase components customary for the pharmaceutical forms according to the invention (ointments, pastes emulsions and especially creams) can be used, and especially the components customary for the preparation of dermatics. As a main component for the preparation of the fatty phase base (ointment base), according to the invention preferably polyethylene wax dispersion on the basis of polyethylene and mineral oil is applied, e.g. Polycos 20 (available from the firm Croda GmbH, 4054 Nettetal). Further fatty phase components preferred according to the invention (as oil components) are triglycerides, preferably medium-chained C 8 to C 10-triglycerides, such as e.g. Miglyol'812 (available from Dynamit Nobel, Troisdorf) and/or 2-octyl-dodecanol. The composition according to the invention preferably contains a mixture of polyethylene wax dispersion and middle-chained triglycerides. The fatty phase (oil phase) further contains additional customary components, such as emulsifiers, stabilizers, antioxidants, penetration. enhancers, penetration-accelerating agents, solubilizers, preservation agents, emulsion stabilizers, etc.

According to the invention, conventional W/O emulsifiers are used as emulsifiers, preferably non-ionogenic emulsifiers, such as e.g. higher fatty alcohols and sterol alcohols, partial fatty acid esters of multivalent alcohols, partial fatty acid esters of sorbitane, sorbitol ethers of polyoxyethylene, fatty alcohol ethers of polyoxyethylene, fatty acid esters of polyglycerol. The choice of suitable emulsifiers is directed especially according to the HLB value (Hydrophylic Lypophilic Balance), whereby essentially HLB values of from 3 to 10, especially from 3 to 6 are applied, such as typically used in W/O-emulsions (see R. Voigt, "Lehrbuch der Pharmazeutischen Technologie", published by Verlag Chemie, Weinheim-New York 1979, pages 358 to 366; H. Sucker, P. Fuchs and P. Speiser, "Pharmazeutische Technologie", published by Georg Thieme Verlag, Stuttgart 1978, pages 300 to 305).

Especially preferred as an emulsifier according to the invention is glycerine sorbitaneoleostearate (a mixture of partial esters of glycerine and sorbitane including the anhydrides thereof with oleostearic acid, which can contain alternating amounts of other fatty acids), e.g. Arlace1,481 (available from the firm ICI).

According to the invention, butyl hydroxyanisol (e.g. Embanox'BHA) is preferably included as a stabilizer/antioxidant; as penetration-enhancing agent which should prepare a dermatophilic slide for lipoid-soluble active ingredients, preferably 2-octyl dodecanol, e.g. Eutanol'G (available from the firm Henkel, Dusseldorf) is included, and/or penetration accelerators for dermal and trans-dermal therapy (see e.g. J: Petersen-Lehmann, "Pharm. Ztg. 134," (1989) 1031–1032, and e.g. propylene glycol and/or medium chained triglycerides, such as e.g. Miglyol'812.

Sorbic acid is preferably included as a preservative agent, and especially a mixture of sorbic acid and propylene glycol. As emulsion stabilizer, preferably magnesium sulfate heptahydrate is included (see e.g. H. G. Wolf, "Pharm. Ztg. 133, (1988) 32).

Besides the above named components, the compositions according to the invention can contain further components, e.g. means for adjusting the pH value, light screening agents, brightening agents, dyes, moisturizers, perfume oils and/or further pharmaceutically inactive ingredients and/or carriers customary for such pharmaceutical preparations. The storage of the compositions according to the invention expediently takes place in tightly sealed containers, cool and light-protected.

The content of piroxicam is especially depending on the pharmaceutical form in which the pharmaceutical compositions according to the invention are present on the basis of a W/O emulsion. As a rule, the compositions according to the invention contain the piroxicam in an amount of 0.1 to 10% by weight, preferably from 0.2 to 5% by weight, and especially in an amount of 0.5 to 1% by weight. Especially preferred embodiments of the compositions according to the invention are W/O creams with a content of 0.5 to 1% by weight piroxicam. Besides the actual active ingredient piroxicam, the compositions can optionally also contain further pharmaceutical effective substances which are compatible with piroxicam in the scope of the application, e.g. further effective substances for the therapy of skin diseases (dermatoses), antibiotics, sulfonamides, disinfecting agents, corticoids, skin care agents and/or means promoting the flow of blood (hyperemising agents) such as e.g. nicotinic acid ester (e.g. benzyl nicotinate), salicylic acid esters (e.g. bornyl salicylate), Extractum Capsici fructus, etheric oils (e.g. pine needle oil).

The oil phase/water phase ratio, and the type and amount of the individual components of the oil- and water phase are especially dependent on the type (pharmaceutical form) of the composition according to the invention, but also on the amount of effective substance and the type of application intended (e.g. for short-term application in the case of injuries, or for longer-term application in the case of rheumatic manifestations).

The fatty phase (oil phase) of the compositions according to the invention preferably includes a mixture of polyethylene wax dispersion (as ointment base), glycerine sorbitaneoleostearate (as emulsifier), 2-octyl-dodecanol and/or medium chained triglycerides, preferably with 8 to 10 carbon atoms (as oil components), and butyl hydroxyanisol (as antioxidant). The compositions according to the invention preferably contain these components in the following amounts: 5 to 30% ointment base, 5 to 25% emulsifier, respectively 0.5 to 15% of one or more oil components, 0.005 to 0.15% antioxidant (the quantitative data relate to % by weight, based on the total composition).

The composition according to the invention is preferably present in the form of a W/O cream. In this case, the weight ratio of oil phase to water phase is expediently 3 to 2.

The water phase preferably contains propyleneglycol (as moisturizer, penetration-enhancer and preservative), sorbic acid (as preservative), magnesium sulfate heptahydrate (as stabilizer), optionally perfume oil and/or further pharmaceutical carriers and/or additives customary for such compositions. The water phase contains the components preferably in the following amounts: 1% to 20% moisturizer/penetration-enhancer, 0.01 to 0.2% preservative, 0.25 to 1.0% stabilizers and 20 to 65% purified water (in % by weight based on the total composition).

The above substances named for the individual components of the compositions according to the invention can however also be replaced by or supplemented by other substances customary for such compositions, especially, by one or more of the following substances:

As ointment base: wool fat, polyethylene with mineral oil, cetyl-palmitate, saturated triglycerides, oleogel DAB9, white petrolatum, yellow petrolatum, ozokerite, a mixture of solid paraffin (micro-wax) and liquid paraffin;

As emulsifier: W/O emulsifiers with HLB values from 3 to 10, especially from 3 to 6, such as primarily mixtures of glycerine fatty acid esters (e.g. glycerine monostearate, -palmitate, -laurate, -myristate and/or -oleate), or glycerine monodi-fatty acid esters (e.g. glycerine monodistearate) or glycerine di-fatty acid esters- (e.g. glycerine dioleate, glycerine distearate) with sorbitane fatty acid esters (e.g. sorbitanemonooleate, -sesquioleate, -trioleate, -stearate, -laurate, -myristate, -palmitate and/or -isostearate);

For the oil components: saturated and unsaturated fatty alcohols with $C_{12}$–$C_{18}$ chain lengths, oleic acid oleyl ester, polyol fatty acid ester, isooctyl stearate, hexyl laurate, di-n-butyladipate, oleyl erucate, capryl/-caprinic acid ester of saturated $C_{12}$–$C_{18}$ fatty alcohols, myristyl myristate, isoadipate, isopropyl palmitate, isopropyl myristate, decyloleate, 2-ethyl hexyl-palmitate, di-(2-ethylhexyl)-adipate, natural oils (e.g. peanut oil, jojoba oil, etc.);

As antioxidants: α-tocopherol (acetate) butyl hydroxytoluene, propyl gallate;

As moisturizer/penetration- enhancer: multivalent alcohols, such as e.g. butandiol, glycerol, sorbitol, pentaerythrol, xylitol;

As preservative: PHB-ester, benzyl alcohol.

The preparation of the compositions according to the invention can take place in a generally known manner customary per se for the preparation of such water-in-oil emulsions, e.g. in the form of pastes, ointments, emulsions or especially in the form of W/O creams. In this connection, the active ingredient (piroxicam) is preferably firstly suspended in a partial amount of the oil components. In an expedient embodiment, firstly a suitable fatty phase is prepared, in which then the active ingredient (piroxicam) is incorporated forming the oil phase, which preferably takes place under heating. The amount of water (water phase) suitable for the desired form of administration is then added under stirring, preferably in the presence of an emulsifier for the formation of a stable emulsion.

If neutral preservatives are used, the aqueous phase is to be adjusted with suitable acids to an acidic pH value (preferably pH=2 to 5).

Since in such emulsions the possibility of the growth of microorganisms exists, it is useful to sterilely prepare and/or to preserve the compositions according to the invention. On account of the process of production, it is possible to achieve the sterility of the composition e.g. in a simple manner by heating the fatty/oil phase, because for the composition and efficacy of the drug according to the invention, phase transitions of the active ingredient from one phase to the other which possibly occur, do not play such a significant role.

Subject matter of the invention is therefore also a process according to claim 21 for the production of a composition according to the invention, which is characterized in that the active ingredient (piroxicam) is incorporated in the oil phase, which is then homogenized with the water phase.

An expedient configuration of this process is the subject matter of claim 22.

The piroxicam is preferably suspended in a middle-chained C 8 to C 10-tritilyceride, and this suspension then stirred into the molten fatty phase for the formation of the oil phase. The composition of the fatty phase (oil phase) and the water phase preferably conforms with the compositions given above for the fatty phase and the water phase.

The following examples describe compositions according to the invention and the process for their production, without limiting the invention to these embodiments. In the above and the following, the percentage and quantitative data are based on the weight, unless otherwise given.

EXAMPLES

Example 1

Preparation of a W/O cream with 0.5% by weight piroxicam.

| Component | Amount in g |
|---|---|
| Polyethylene wax dispersion (Polycos '20) | 20.0 |
| Glycerine-sorbitaneoleostearate (Arlacel '481) | 11.0 |
| 2-octyl-dodecanol (Eutanol 'G) | 5.0 |
| Butyl hydroxyanisole (Embanox 'BHA) | 0.01 |
| Medium-chained triglycerides (Miglyol '812) | 5.0 |
| Piroxicam | 0.5 |
| Propylene glycol | 10.0 |
| Sorbic acid | 0.01 |
| Magnesium sulfate.7H2O | 0.07 |
| Perfume oil | 0.09 |
| Purified water | 46.6 |
| Preparation | 100.0 g |

The cream is prepared by the following process steps:

1. The above-named components Polycos, Arlacel, Eutanol, Miglyol (4.0 g) and Embanox are melted in a VA-vessel under stirring at 80° C., so that special attention is paid to the complete melting of Arlacel;

2. The sorbic acid is dissolved in propylene glycol at about 55° C.;

3. The water is heated in a VA vessel to 65° to 70° C., the magnesium sulfate then dissolved. Thereafter the sorbic acid solution previously prepared under step 2 is stirred in; the temperature of the water phase thus prepared should be 65° C.;

4. The piroxicam is suspended in Miglyol (1.0 g) with a high-speed stirring device, and this suspension then added to the molten fatty phase and shortly stirred in;

5. The water phase prepared under step 3, is added to the fatty phase, emulsified and homogenized;

6. The emulsified homogenate is cold-stirred under vacuum, the perfume then added at 40° C., then cold-stirred without vacuum, and the vessel emptied at 28° to 30° C.

A stability examination extending over 21 months on 2 batches of the prepared cream showed a slight yellowing, complying with the scope of the specification. Yellow dots, such as those occurring in O/W creams by formation of the yellow piroxicam monohydrate, were not recognized. The current stability examination revealed the W/O cream to be a stable pharmaceutical form for piroxicam.

Example 2

According to the process described in example 1, the following composition was prepared.

| Component | Amount in g |
|---|---|
| Wool fat | 5.0 |
| Polyethylene wax dispersion | 10.0 |
| Isopropyl myristate | 15.0 |
| Sorbitanesesquioleate | 6.5 |
| White petrolatum | 16.0 |
| Piroxicam | 1.0 |
| Sorbitol solution 70% | 6.5 |
| Sorbic acid | 0.15 |
| Purified water | 39.85 |
| Preparation | 100.00 g |

A stability examination of this composition revealed the same good results as the composition according to example 1.

Example 3

According to the process given in example 1, the following composition was prepared:

| Component | Amount in g |
|---|---|
| Wool fat | 10.0 |
| mineral oil | 15.0 |
| Polyethylene | 4.0 |
| Isopropyl myristate | 10.0 |
| Sorbitanetrioleate | 6.5 |
| White petrolatum | 10.0 |
| Piroxicam | 1.0 |
| Propylene glycol | 3.0 |
| Sorbic acid | 0.15 |
| Purified water | 40.35 |
| Preparation | 100.00 g |

The stability of this composition was comparable with that of the compositions of Examples 1 and 2.

Example 4

The "Piroxicam-Creme" produced in Example 1 (effective content 0.5% by wt.) was examined for its antiphlogistic effect and compared with a comparative preparation (gel from propylene glycol, ethyl- and benzyl alcohol with 0.5 % by wt. piroxicam).

The antiphlogistic effect was examined on the UV-induced erythema of the guinea pig (10 animals per group respectively).

The shaved skin of the back of the guinea pig was subjected to UV-B-light (280 to 315 nm) for 1 minute to cause the erythema. Subsequently 50 mg of the respective preparations was applied to the irradiated location.

The 0.5% "Piroxicam-Creme" (according to the invention hindered the intensity of the erythema by an amount between 27.8% and 60%, the maximum inhibition effect occurring 2 hours post-administration (p.a.). The comparative preparation (gel) revealed an inhibition effect of between 13.3% and 66.7%, the maximum being after 1 hour p.a., where also in the control group the erythema had still not yet reached its full intensity. At later examination times, the inhibition effect of the comparative preparation was of weaker intensity than of the "Piroxicam-Creme" of the invention.

With a "Piroxicam-Creme" according to the invention, which contained 1% by wt. active ingredient (piroxicam), similar inhibition effects (between 22.2% and 60.0%) were determined, the maximum also being registered 2 hours p.a.

Significant reductions of the frequency of erythema (results $\geq 2$) were registered in the group which was treated with 0.5% "Piroxicam-Creme" 4 hours p.a., in the group which was treated with 1% "Piroxicam-Creme" 3 hours after the application in comparison to the control group (placebo-group).

The results obtained in the above examination clearly show the intense antiphlogistic effect of the W/O creams according to the invention, whereby the antiphlogistic effect of the comparative preparation according to the prior art (gel) is additionally exceeded with respect to the duration of the efficacy.

Subject matter of the filed invention is therefore also the use of a pharmaceutical composition according to the invention as anti-rheumatic, antiphlogistic and/or antiinflammatory pharmaceutical for the treatment of respective diseases.

The type, dose and frequency of the topical administration mainly depends on the severity of the disease and the general condition of the patient, but also on the condition and sensitivity of the skin. As a rule, the administration corresponds to the usual conditions for such compositions.

Having described the invention above, various modifications of the techniques, procedures, material and equipment will be apparent to those in the art. It is intended that all such variations within the scope and spirit of the appended claims be embraced thereby.

We claim:

1. Pharmaceutical composition for topical application comprising a water in oil emulsion, characterized in that said emulsion contains a therapeutically effective amount of piroxicam in the oil phase as the active ingredient.

2. Composition according to claim 1, characterized in that the oil phase contains a polyethylene wax dispersion.

3. Composition according to claim 2, characterized in that the oil phase contains as a penetration enhancer medium-chained triglycerides, 2-octyl-dodecanol, or mixtures thereof.

4. Composition according to claim 1, characterized in that the oil phase contains as a penetration-enhancing agent, medium-chained triglycerides, 2-octyldodecanol, or mixtures thereof.

5. Composition according to claim 1, characterized in that said composition contains one or more of emulsifiers, stabilizers, antioxidants, solubilizers, penetration enhancers, penetration-accelerating agents, preservatives, emulsion stabilizers and perfume.

6. Composition according to claim 5, characterized in that said composition contains as emulsifier one or more emulsifiers with a HLB value of from 3 to 6.

7. Composition according to claim 6, characterized in that said composition contains as an emulsifier one or more of glycerine-sorbitane fatty acid esters, sorbitane fatty acid esters, glycerine fatty acid esters, glycerine monodi-fatty acid esters and glycerine di-fatty acid esters.

8. Composition according to claim 7, characterized in that said composition contains as emulsifier glycerine-sorbitane oleostearate.

9. Composition according to claim 5, characterized in that said composition contains one or more of glycerine-sorbitaneoleostearate, butyl hydroxyanisole 2-octyl dodecanol, propylene glycol and magnesium sulfate heptahydrate.

10. Composition according to claim 5, characterized in that said composition contains sorbic acid or a mixture of sorbic acid and propylene glycol as a preservative.

11. Composition according to claim 1 characterized in that said composition contains piroxicam in an amount of 0.1 to 10% by weight.

12. Composition according to claim 11, characterized in that said composition contains the piroxicam in an amount of 0.2 to 5% by weight.

13. Composition according to claim 12, characterized in that said composition contains piroxicam in an amount of 0.5 to 1% by weight.

14. Composition according to claim 1, characterized in that said composition is in the form of a water in oil-cream.

15. Composition according to claim 14, characterized in that said composition comprises a molten mixture of an ointment base, an oil component, an emulsifier, and an antioxidant,
wherein said ointment base contains one or more of a polyethylene wax dispersion, wool fat, white petrolatum, and polyethylene with mineral oil,
said oil component contains one or more of isopropyl myristate, 2-octyl-dodecanol, and medium-chained triglycerides,
said emulsifier contains one or more of glycerine-sorbitane fatty acid esters, sorbitane fatty acid esters, glycerine fatty acid esters, glycerine monodi-fatty acid esters and glycerine di-fatty acid esters and
said antioxidant contains one or more of alpha-tocopherol acetate, butyl hydroxytoluene, propyl gallate, and butyl hydroxyanisole.

16. Composition according to claim 15, characterized in that the oil phase of said molten mixture contains polyethylene wax dispersion, 2-octyldodecanol, medium-chained triglycerides, glycerine sorbitane oleostearate, and butyl hydroxyanisole.

17. Composition according to claim 14, characterized in that said composition contains 5 to 30% ointment base, 5 to 25% emulsifier, respectively 0.5 to 15% of one or more oil components and 0.005 to 0.15% antioxidant, based on the weight of the total composition.

18. Composition according to claim 14, characterized in that the ratio of the weights of the oil phase to water phase amounts to approximately 3 to 2.

19. Composition according to claim 14, characterized in that the water phase contains one or more of glycerol, sorbitol, pentaerythrol, xylitol, and propylene glycol.

20. Composition according to claim 14, characterized in that the water phase contains one or more of preservatives and stabilizers.

21. Composition according to claim 20, characterized in that the water phase contains one or more of sorbic acid and magnesium sulfate heptahydrate.

22. Composition according to claim 11, characterized in that the water phase contains 1 to 20% moisturizer/penetration-enhancer, based on the weight of the total composition.

23. Composition according to claim 22 further containing 0.01 to 0.2% preservative, based on the total weight of the composition.

24. Composition according to claim 23, further containing 0.25 to 1.0% stabilizer, based on the weight of the total composition.

25. Composition according to claim 22 further containing 0.25 to 1.0% stabilizer, based on the weight of the total composition.

26. Composition according to claim 1, characterized in that said composition contains as ointment base one or more of polyethylene wax dispersion, wool fat, white petrolatum and polyethylene with mineral oil.

27. Composition according to claim 1, characterized in that said composition contains as oil component one or more of medium-chained triglycerides, 2-octyl dodecanol and isopropyl myristate.

28. Process for producing a water in oil emulsion having a water phase and an oil phase, and having piroxicam in the oil phase, said process comprising the steps of:
heating an oil phase to produce a molten, heated oil phase;
incorporating piroxicam into the molten, heated oil phase; and
heating a water phase to produce a heated water phase; and
homogenizing the molten, heated oil phase with the heated water phase.

29. Process according to claim 28, characterized in that the piroxicam is suspended in an oil component and this suspension is stirred into a molten, heated fatty acid phase to form the oil phase, and this is then homogenized with the heated water phase.

30. Method for treating an individual suffering from a rheumatic, antiphlogistic or inflammatory condition comprising topically administering a therapeutic dose of a water in oil emulsion having piroxicam in the oil phase.

* * * * *